US010099211B2

(12) United States Patent
Knott et al.

(10) Patent No.: US 10,099,211 B2
(45) Date of Patent: Oct. 16, 2018

(54) PROCESS FOR PRODUCING COMPOSITIONS COMPRISING PLATINUM

(71) Applicant: Evonik Degussa GmbH, Essen (DE)

(72) Inventors: Wilfried Knott, Essen (DE); Klaus-Dieter Klein, Muelheim an der Ruhr (DE); Horst Dudzik, Essen (DE)

(73) Assignee: Evonik Degussa GmbH, Essen (DE)

( * ) Notice: Subject to any disclaimer, the term of this patent is extended or adjusted under 35 U.S.C. 154(b) by 62 days.

(21) Appl. No.: 14/939,687

(22) Filed: Nov. 12, 2015

(65) Prior Publication Data

US 2016/0130290 A1    May 12, 2016

(30) Foreign Application Priority Data

Nov. 12, 2014  (EP) .................... 14192830

(51) Int. Cl.
  *C07F 15/00*  (2006.01)
  *B01J 31/22*  (2006.01)
  *C08G 77/46*  (2006.01)
  *C08G 77/08*  (2006.01)

(52) U.S. Cl.
  CPC ........... *B01J 31/2295* (2013.01); *C07F 15/00* (2013.01); *C08G 77/08* (2013.01); *C08G 77/46* (2013.01); *B01J 2231/323* (2013.01); *B01J 2531/828* (2013.01)

(58) Field of Classification Search
  CPC ... B01J 31/2295; C07F 15/0086; C07F 15/00; C08G 77/08; C08G 77/46
  USPC .......................................... 556/136; 502/152
  See application file for complete search history.

(56) References Cited

U.S. PATENT DOCUMENTS

| | | | |
|---|---|---|---|
| 4,276,252 A | 6/1981 | Kreis et al. |
| 5,371,161 A | 12/1994 | Knott |
| 5,430,166 A | 7/1995 | Klein et al. |
| 5,430,167 A | 7/1995 | Klein et al. |
| 5,455,367 A | 10/1995 | Klein et al. |
| 5,475,127 A | 12/1995 | Klein et al. |
| 5,486,634 A | 1/1996 | Hahn et al. |
| 5,856,548 A | 1/1999 | Dröse et al. |
| 6,255,511 B1 | 7/2001 | Klein et al. |
| 6,291,622 B1 | 9/2001 | Dröse et al. |
| 6,307,082 B1 | 10/2001 | Klein et al. |
| 6,489,498 B2 | 12/2002 | Klein et al. |
| 6,854,506 B2 | 2/2005 | Knott et al. |
| 6,858,663 B2 | 2/2005 | Knott et al. |
| 6,915,834 B2 | 7/2005 | Knott et al. |
| 7,018,458 B2 | 3/2006 | Knott et al. |
| 7,125,585 B2 | 10/2006 | Dudzik et al. |
| 7,157,541 B2 | 1/2007 | Knott et al. |
| 7,612,159 B2 | 11/2009 | Burkhart et al. |
| 7,619,035 B2 | 11/2009 | Henning et al. |
| 7,645,848 B2 | 1/2010 | Knott et al. |
| 7,754,778 B2 | 7/2010 | Knott et al. |
| 7,825,205 B2 | 11/2010 | Knott et al. |
| 7,825,206 B2 | 11/2010 | Neumann et al. |
| 7,825,209 B2 | 11/2010 | Knott et al. |
| 8,138,294 B2 | 3/2012 | Henning et al. |
| 8,247,525 B2 | 8/2012 | Schubert et al. |
| 8,283,422 B2 | 10/2012 | Schubert et al. |
| 8,309,664 B2 | 11/2012 | Knott et al. |
| 8,334,355 B2 | 12/2012 | Henning et al. |
| 8,349,907 B2 | 1/2013 | Henning et al. |
| 8,420,748 B2 | 4/2013 | Henning et al. |
| 8,455,603 B2 | 6/2013 | Ferenz et al. |
| 8,557,944 B2 | 10/2013 | Henning et al. |
| 8,598,295 B2 | 12/2013 | Henning et al. |
| 8,623,984 B2 | 1/2014 | Henning et al. |
| 8,722,836 B2 | 5/2014 | Knott et al. |
| 8,729,207 B2 | 5/2014 | Hartung et al. |
| 8,772,423 B2 | 7/2014 | de Gans et al. |
| 8,779,079 B2 | 7/2014 | Henning et al. |
| 8,802,744 B2 | 8/2014 | Knott et al. |
| 8,841,400 B2 | 9/2014 | Henning et al. |
| 8,921,437 B2 | 12/2014 | Knott et al. |

(Continued)

FOREIGN PATENT DOCUMENTS

EP    0011714 A2    6/1980

OTHER PUBLICATIONS

Otto et al., Inorganic Chemistry Communications, vol. 9, pp. 764-766 (2006).*
Szuromi et al. J Amer. Chem. Soc., 2006, 128(37), 12088-12089.*
He et al. Can. J. Chem., 2003, 81(7), 861-867.*
Still et al. J Amer. Chem. Soc., 1966, 88(22), 5135-5141.*
Szuromi et al. J Amer. Chem. Soc., 2006, 128(37), 12088-12089. (Year: 2006).*
Noll, W., "Chemie Und Technologie Der Silicone", 1960, Verlag Chemie, Weinheim/Bergstr., pp. 20-51.

(Continued)

*Primary Examiner* — Clinton A Brooks
*Assistant Examiner* — Kofi Adzamli
(74) *Attorney, Agent, or Firm* — Nexsen Pruet, PLLC; Philip P. McCann

(57) ABSTRACT

The invention relates to a process for producing preparations including one or more mononuclear platinum complex compounds of formula (X), one or more compounds comprising carbon atoms, hydrogen atoms and at least two oxygen atoms as compound(s) from compound class II, and one or more olefinically unsaturated compound(s) selected from olefin1 and olefin2 as compound(s) from compound class III, by contacting at least one compound from each of compound classes II and III with one or more dinuclear platinum (II) compound(s) as compound(s) from compound class I. The process includes performing a first step of preparing a mixture by adding together at least two compounds selected from two different compound classes and a subsequent step of admixing the mixture obtained in the first step with one or more compounds of the still absent compound class.

19 Claims, No Drawings

(56) References Cited

U.S. PATENT DOCUMENTS

| | | |
|---|---|---|
| 8,946,369 B2 | 2/2015 | Henning et al. |
| 8,957,009 B2 | 2/2015 | Schubert et al. |
| 8,974,627 B2 | 3/2015 | Schubert et al. |
| 8,993,706 B2 | 3/2015 | Schubert et al. |
| 9,035,011 B2 | 5/2015 | Ferenz et al. |
| 9,068,044 B2 | 6/2015 | Schubert et al. |
| 2002/0161158 A1 | 10/2002 | Burkhart et al. |
| 2007/0128143 A1 | 1/2007 | Gruning et al. |
| 2008/0227923 A1 | 9/2008 | Klein et al. |
| 2010/0022435 A1 | 1/2010 | Henning et al. |
| 2011/0046305 A1 | 2/2011 | Schubert et al. |
| 2011/0230619 A1 | 9/2011 | Kuppert et al. |
| 2011/0301254 A1 | 12/2011 | Knott et al. |
| 2012/0068110 A1 | 3/2012 | Schubert et al. |
| 2012/0282210 A1 | 11/2012 | Henning et al. |
| 2013/0041115 A1 | 2/2013 | Knott et al. |
| 2013/0213267 A1 | 8/2013 | Fiedel et al. |
| 2013/0345318 A1 | 12/2013 | Schubert et al. |
| 2014/0256844 A1 | 9/2014 | Henning et al. |
| 2014/0309446 A1 | 10/2014 | Amajjahe et al. |
| 2015/0004112 A1 | 1/2015 | Ritter et al. |
| 2015/0004113 A1 | 1/2015 | Ritter et al. |
| 2015/0023900 A1 | 1/2015 | Knott et al. |
| 2015/0057412 A1 | 2/2015 | Knott et al. |
| 2015/0080593 A1 | 3/2015 | Henning et al. |

OTHER PUBLICATIONS

Steffanut, P., et al., "Efficient Homogenous Hydrosilylation of Olefins by Use of Complexes of Pt° with Selected Electron-Deficient Olefins as Ligands", Chem. Eur. J., Oct. 2, 1998, vol. 4, No. 10, pp. 2008-2017.

Johnson Matthey Handbook of Pharmaceutical Catalysis, 2009, p. 46.

\* cited by examiner

PROCESS FOR PRODUCING COMPOSITIONS COMPRISING PLATINUM

FIELD OF THE INVENTION

The present invention relates to a process for producing preparations comprising one or more mononuclear platinum complex compounds of formula (X), as defined below, one or more compounds comprising carbon atoms, hydrogen atoms and at least two oxygen atoms as a compound(s) from compound class II, and one or more olefinically unsaturated compound(s) selected from olefin1 and olefin2 as a compound(s) from compound class III. The present invention also relates to a preparation obtainable by this process and to the use thereof.

BACKGROUND OF THE INVENTION

SiC-bonded organomodified siloxanes, especially polyether siloxanes, are an industrially important substance class given their widely adjustable surfactant properties. The established route to producing these substances is the platinum metal-catalyzed addition of siloxanes and silanes bearing SiH groups onto olefinically functionalized compounds, for example onto allyl polyethers.

The use of platinum catalysts for the addition of silanes or siloxanes comprising SiH groups onto compounds comprising one or more olefinic double bonds is known (hydrosilylation) and is described, for example, in "Chemie and Technologie der Silicone", Verlag Chemie, 1960, page 43, and in the patent literature, for example in DE-A-26 46 726, EP-A-0 075 703 and U.S. Pat. No. 3,775,452. In current industrial practice, predominantly hexachloroplatinic acid and cis-diammineplatinum(ll) chloride have become established.

Platinum catalysts often employed in the more recent past are Karstedt-type catalysts (see, for example, U.S. Pat. No. 3,814,730). These platinum catalysts are prone to deactivation and shut-down phenomena when employed in the production of organomodified siloxanes, in particular allyl polyether siloxanes, and the addition reaction thus often requires postcatalysis and/or even drastic increases in temperature.

WO-A-98/00463 describes defined solid compounds having high decomposition temperatures (144.3° C. and 138.4° C.) which by addition of selected electron-poor olefins to a Karstedt catalyst are said to provide an active and simultaneously stable catalyst system for homogeneous hydrosilylation. The enhanced activity is attributed to the introduction of strongly π-acidic ligands, such as, in particular, methylnaphthoquinone and tetraethyltetracarboxylatoethylene. The reported examples comprise adding triethylsilane onto vinyltrimethylsilane, a 100% excess of the olefin component being employed. Despite the large excess and taking into account that the vinyl group, in contrast to the allyl group, is not isomerization-active, at 50° C., this catalysis shuts down due to deactivation after 2 hours to achieve an SiH conversion of only 68%. At 73° C., this catalyst system decomposes immediately giving an SiH conversion of only 18% (P Steffanut et al., Chem. Eur. J. 1998, 4, No. 10, page 2014).

EP 1 520 870 describes a catalyst which overcomes several of the cited problems. The catalyst is produced by admixing platinum$^{(0)}$ complex catalyst solutions, in particular those based on commercially available Karstedt complexes, with effective amounts of activating $C_{2-6}$ olefins before adding these to the hydrosilylation matrix and then carrying out the hydrosilylation at moderate temperatures, preferably at between about 20° C. and about 150° C.

Unpublished application DE 102014213507.9 describes that obtaining storage-stable preparations, particularly when using di-μ-chlorobis[chloro(cyclohexene)platinum(H)] (Pt 92), requires contacting the platinum compound with at least one compound comprising at least two oxygen atoms and also having a measurable olefinic unsaturation content.

In U.S. Pat. No. 3,516,946 Modic describes that catalysts, which may be used advantageously in the production of silicone rubbers (LSR systems), are obtainable by reacting complexes of the type $[PtCl_2$ olefin$]_2$ or $H[PtCl_2$ olefin] with a cyclic alkylvinylpolysiloxane of formula $[(CH_2=CH)(R) SiOl_n$, to bring about thermal elimination and displacement of the olefin present in the starting complexes. The synthesis of these particular catalysts is time-consuming and, even in the case of easily displaced ethylene, necessitates a reaction performed at 60° C. over six hours. Cyclohexene, which is more difficult to substitute, is likewise estimated to require six hours, but at 70° C. From a commercial practice standpoint this method provides neither a simple, nor, a cost-effective route to novel catalyst systems.

SUMMARY OF THE INVENTION

The present invention provides a simple process for producing preparations which comprise one or more platinum (II) compounds. Such preparations have the greatest possible storage stability.

The present invention provides a process for producing preparations comprising one or more platinum (II) compounds as compound(s) from compound class I, one or more compounds which comprise carbon atoms, hydrogen atoms and at least two oxygen atoms and may optionally comprise an olefinic unsaturation as compound(s) from compound class II, and one or more olefinically at least monounsaturated compound(s) comprising fewer than two oxygen atoms as compound(s) from compound class III. The inventive process includes producing the composition by performing a first step of preparing a mixture by adding together at least two compounds selected from two different compound classes mentioned above and a subsequent step of admixing the mixture obtained in the first step with one or more compounds of the absent compound class mentioned above.

The present invention provides a preparation obtainable by this process and the use of the preparation preferably as catalyst in a process where compounds comprising H—Si groups are reacted with compounds comprising olefinic double bonds.

The preparations according to the present invention have the advantage that they permit dust-free storage and metered addition of the often toxic and/or carcinogenic catalyst.

Addition of the catalyst in the form of the preparation of the present invention has the further advantage that it permits more precise metered addition of the catalyst to the reaction mixture since the build up of dusty deposits on pipes or the like is prevented.

DETAILED DESCRIPTION OF THE INVENTION

Surprisingly to those skilled in the art stabilization of the preparations according to the present invention requires only a small molar excess of olefin based on the platinum employed. Thus, for example, stabilizing a preparation comprising 0.6 weight percent of platinum in butyl diglycol for one week requires an addition of only double the molar amount of cyclohexene based on the total molar amount of platinum in the di-µ-chlorobis[chloro(cyclohexene)platinum (II)] (Pt 92). Without the cyclohexene addition, the di-µ-chlorobis[chloro(cyclohexene)platinum(II)] (Pt 92) preparation in butyl diglycol suffers from degradation with precipitation of platinum even after one day of storage in the absence of light (Example 1).

Depending on the platinum compound employed, the use of the preparation according to the present invention can enhance activity, apparent from a relatively early clearing point and measurable as SiH conversion as a function of time, compared to customary pulverulent catalysts in hydrosilylation reactions.

Employing the preparations comprising platinum (II) compounds of relatively high valence is advantageous for the quality of the desired SiC bond forming products, in particular of the polyether siloxanes, which are used as polyurethane foam stabilizers or as coatings additives for example, since the use of said preparations in batch processes avoids local overconcentrations of platinum at the introduction point of the hydrosilylation reactor which may cause undesired platinum precipitation and gel formation.

The process according to the present invention for producing the preparations, the preparations according to the present invention and the use thereof according to the present invention are described below by way of example, without any intention that the invention be limited to these illustrative embodiments. Where ranges, general formulae or compound classes are specified hereinbelow, these are intended to include not only the relevant ranges or groups of compounds explicitly mentioned but also all subranges and subgroups of compounds that may be obtained by extracting individual values (ranges) or compounds. Where documents are cited in the context of the present description, their content shall fully belong to the disclosure content of the present invention particularly in respect of the factual position in the context of which the document was cited. Percentages specified hereinbelow are by weight unless otherwise stated. Average values specified hereinbelow are number averages unless otherwise stated. Where properties of a material are referred to hereinbelow, for example viscosities or the like, these are properties of the material at 25° C. unless otherwise stated. When chemical (empirical) formulae are used in the present invention, the reported indices may be either absolute numbers or averages. Indices relating to polymeric compounds are preferably average values.

The process according to the present invention provides preparations that comprise one or more mononuclear platinum complex compounds of formula (X)

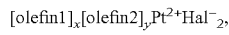
[olefin1]$_x$[olefin2]$_y$Pt$^{2+}$Hal$^-_2$, where Hal=F, Cl, Br or I, more preferably Cl, Br or I, an even more preferably Cl, x=1 or 2, y=0 or 1, olefin1=a compound comprising at least one olefinic unsaturation, fewer than two oxygen atoms and preferably no silicon atom, olefin2=a compound comprising an olefinic unsaturation, fewer than two oxygen atoms and preferably no silicon atom, with the proviso that when olefin1 comprises at least two olefinic unsaturations, x=1, and x+y=1 and when olefin1 comprises only one olefinic unsaturation, x+y=2, one or more compounds comprising carbon atoms, hydrogen atoms and at least two oxygen atoms and optionally comprising one or more, preferably one, olefinic unsaturation(s) as compound (s) from compound class II, and one or more olefinically unsaturated compound(s) selected from olefin1 and olefin2 as compound(s) from compound class III. The process of the present invention comprises contacting a compound from each of compound classes II and III with one or more dinuclear platinum (II) compound(s) as compound(s) from compound class I. Specifically, the process of the present invention comprises performing a first step of preparing a mixture by adding together at least two compounds selected from two different compound classes. In a subsequent step the mixture obtained in the first step is admixed with one or more compounds of the still absent compound class.

As compounds from compound class III, i.e., as olefin2 and olefin1, which comprises only one olefinic unsaturation, identical or different compounds preferably selected from olefinically monounsaturated hydrocarbons comprising 2 to 30 carbon atoms which may optionally bear on the olefinic double bond, not only hydrogen, but also further substituents, for example aliphatic, cycloaliphatic and/or aromatic radicals, hydroxy, hydroxyalkyl, silyl and/or siloxanyl groups, may be present/employed. It is preferable when olefin2 and olefin1 which comprises only one olefinic unsaturation are selected from allyl alcohol, alkenols, for example butenols, pentenols, hexenols, alkenes, in particular ethylene, propene, 1-butene, cis-butene, trans-butene, isobutene, pentene, hexene, octene, nonene, decene, undecene, dodecene, cyclopentene, vinylcyclohexane, allyl chloride, methallyl chloride, methallyl alcohol, styrene, α-methylstyrene, indene, cis-stilbene, trans-stilbene and 1,1-diphenylethene. It is preferable when olefin2 and olefin1 which comprises only one olefinic unsaturation are ethylene or cyclohexene. It is more preferable when olefin2 or olefin1 which comprises only one olefinic unsaturation.

As olefin1 which comprises at least two olefinic unsaturations any compounds comprising at least two olefinic unsaturations which are nonconjugated may be present/employed. Preference is given to the compounds selected from 1,5-cyclooctadiene, norbornadiene, 1,3-divinyl-1,1,3, 3-tetramethyldisiloxane, 1,5-hexadiene, 1,2-divinylcyclohexane, 1,2-divinylbenzene, dicyclopentadiene and diallyl ether.

Producing the preparation preferably comprises a first step of preparing a mixture of compounds from compound classes I and III and a subsequent step of admixing the mixture obtained in the first step with compound(s) from compound class II or it comprises a first step of preparing a mixture of compounds from compound classes II and III and a subsequent step of admixing the mixture obtained in the first step with compound(s) from compound class I.

It is preferable when the first step does not comprise preparing a mixture comprising the compounds from compound classes I and II.

Producing the preparations according to the invention may require handling and mixing of gases, liquids and/or solids in the individual steps of the sequential production. The mixing may be achieved in any conceivable fashion. Preference is given to short-duration introduction using conventional stirring means.

The process according to the invention is preferably carried out such that the amount of compounds from compound class I employed is such that the proportion of compounds from compound class I based on the sum of the employed compounds from compound classes I, II, and III is from 0.1 to 50.0 wt %, by preference from 0.2 to 25 wt %, preferably from 0.3 to 10 wt % and more preferably from 0.3 to 1.0 wt %.

The employed amount of compounds from compound class III is preferably selected such that the preparation has an olefinic unsaturation content of at least 0.05 g of iodine/ 100 g of preparation, corresponding to at least 0.002 meq/g.

The olefinic unsaturation content may be determined by iodometric means or alternatively by quantitative $^1$H NMR spectroscopy. An example of a suitable method of determining the content of olefinically unsaturated polyoxyalkylene compounds is the Hanus method for iodine number determination which is familiar to those skilled in the art and known as method DGF C-V 11 a (53) of the German Society of Fat Science. The iodine number according to DGF C-V 11 a (53) indicates the concentration of double bonds in a defined weight quantity of a substance. Also suitable is ASTM test method D-2849-69. Quantitative $^1$H NMR spectroscopy is particularly suitable for precise determination of very small contents of olefinically unsaturated groups in polyoxyalkylenes, particularly when an internal standard is added to the sample to be analyzed. High-resolution NMR instruments can be used to quantitatively determine the proportions of the olefinically unsaturated groups present in the sample and accordingly to report the proportions as the iodine number equivalent. NMR spectroscopy is an efficient method for characterizing organometallic compounds such as the mononuclear platinum complex compounds of formula (X) for example. $^1$H, $^{13}$C and $^{195}$Pt NMR spectroscopy may be used to characterize the platinum-bonded olefinic ligands and the bonding scenarios thereof. Chemical shift values may be used to distinguish between free and bonded ligands and to quantify the respective proportions thereof. The platinum-carbon and platinum-hydrogen couplings may be used to achieve one-to-one assignment of the π-ligands interacting with the metal center.

The compounds from compound class II that may be employed in the process according to the invention may comprise one or more olefinic unsaturations or may be free of olefinic unsaturations. It is also possible to employ in the process according to the invention mixtures of compounds from compound class II that comprise compounds from compound class II comprising one or more olefinic unsaturations and compounds from compound class II that are free from olefinic unsaturations. The process according to the invention preferably employs as compounds from compound class II compounds of formula (IV)

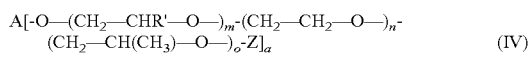

A[-O—(CH$_2$—CHR'—O—)$_m$-(CH$_2$—CH$_2$—O—)$_n$-(CH$_2$—CH(CH$_3$)—O—)$_o$-Z]$_a$     (IV)

where
A is either hydrogen or an at least one carbon atom-comprising saturated or unsaturated organic radical, preferably an at least one carbon atom-comprising organic radical of an organic starter compound for preparing the compound, more preferably a methyl, ethyl, propyl, butyl, vinyl or allyl group,
R' is independently at each occurrence a saturated 2-18 carbon atom-comprising alkyl group or an aromatic radical, preferably an ethyl group or a phenyl radical respectively,
Z is either hydrogen, a linear or branched, saturated or unsaturated 1-18 carbon atom-comprising hydrocarbon radical, preferably a methyl, ethyl, propyl, butyl, vinyl or allyl group, or
the radical of an organic acid of formula —C(=O)—Z$_E$, where Z$_E$ is an organic radical, preferably a linear or branched, saturated or olefinically unsaturated 1 to 17 carbon atom-comprising hydrocarbon radical, preferably a methyl group, or an aromatic 6 to 20 carbon atom-comprising hydrocarbon radical, preferably a phenyl radical, or
the radical of formula —C(=O)—O—Z$_C$, where Z$_C$ is an organic radical, preferably a linear or branched, saturated or olefinically unsaturated 1 to 18 carbon atom-comprising hydrocarbon radical, preferably a methyl group, ethyl group, or an aromatic 6 to 20 carbon atom-comprising hydrocarbon radical, preferably a phenyl radical,
m equals 0 to 50, preferably 0 to 30, more preferably 0 to 20,
n equals 0 to 250, preferably 3 to 220, more preferably 5 to 200,
equals 0 to 250, preferably 3 to 220, more preferably 5 to 200,
a equals 1 to 8, preferably more than 1 to 6, more preferably 1, 2, 3 or 4,
with the proviso that m, n and o sum to no less than 1.

It is preferable to employ compounds of formula (IV) comprising exclusively hydrogen atoms, oxygen atoms and carbon atoms.

The index values recited in the present application and the value ranges of the indices specified may be understood as meaning averages (weight averages) of the possible statistical distribution of the structures actually present and/or the mixtures thereof. This is also true for the structural formulae which on the face of it have been reproduced in exact terms, for example for formulae (IV) and (VI).

The units labelled m, n, and o may either be statistically mixed or may form a blockwise arrangement in the chain. Statistical distributions may have a blockwise construction with any number of blocks and any sequence or be subject to a randomized distribution, they may also have an alternating construction or form a gradient along the chain, in particular they can also form any hybrid thereof wherein groups of different distributions may follow each other. The statistical distributions may be subject to restrictions resulting from specific embodiments. For all ranges which are not affected by the restriction, there is no change in the statistical distribution.

In the context of the present invention, radical A is preferably to be understood as meaning radicals of substances forming the start of the compound of formulae (IV) to be prepared which is obtained by addition of alkylene oxides. The starter compound is preferably selected from the group of alcohols, polyetherols and phenols. It is preferable to use as the starter compound comprising the group A a mono- or polyfunctional polyether alcohol and/or a mono- or polyfunctional alcohol or any desired mixtures thereof. In the case where a plurality of starter compounds A were employed as a mixture, the index a may also be subject to a statistical distribution. Z may moreover be the radical of a starter compound Z—OH.

Monomers preferably used in the alkoxylation reaction include ethylene oxide, propylene oxide, butylene oxide and/or styrene oxide and also any desired mixtures of these epoxides. The different monomers may be used in pure form or as a mixture. It is also possible to effect continuous metered addition over time of a further epoxide into an epoxide already present in the reaction mixture in order to bring about an increasing concentration gradient of the continuously added epoxide. The polyoxyalkylenes formed are thus subject to a statistical distribution in the end product, restrictions being determinable via the metered addition. In the case referred to here of continuous addition of a further epoxide to an epoxide already present in the reaction mixture, a structure gradient along the length of the chain is to be expected. The correlations between metered addition and product structure are known to those skilled in the art.

It is preferable to employ in the process according to the invention compounds from compound class II having a weight-average molar mass of from 76 to 10 000 g/mol, preferably from 100 to 8000 g/mol and more preferably from 200 to 6000 g/mol.

Compounds from compound class II that may be employed are preferably compounds derived from a compound of formula (VI)

A[-OH]$_a$ (VI)

wherein the radical A derives from compounds selected from the group consisting of mono- and polyfunctional monomers, oligomeric and polymeric alcohols, phenols, carbohydrates and carbohydrate derivatives, where particular preference is given to using compounds of formula (VI) where the radical A derives from one or more alcohols from the group of butanol, 1-hexenol, octanol, dodecanol, stearyl alcohol, vinyloxybutanol, 2-ethylhexanol, cyclohexanol, benzyl alcohol, ethylene glycol, propylene glycol, di-, tri- and polyethylene glycol, 1,2-propylene glycol, di- and polypropylene glycol, 1,4-butanediol, 1,6-hexanediol, trimethylolpropane, glycerol, pentaerythritol, sorbitol, allyl alcohol, vinyl alcohol or from hydroxyl group-bearing compounds based on natural products.

Particular preference is given to using compounds from compound class II that are liquid at a pressure of 101 325 Pa and a temperature of 23° C. Among these, very particular preference is given to butyl diglycol, dipropylene glycol and propylene glycol.

Compounds of formulae (IV) employable in accordance with the invention as compounds from compound class II and processes for the production thereof are described in EP 1 520 870, EP 0 075 703, U.S. Pat. No. 3,775,452 and EP 1 031 603, for example. Suitable processes utilize, for example, basic catalysts, such as alkali metal hydroxides and alkali metal methoxides. The use of KOH is particularly widespread and has been known for many years. Such processes typically comprise reacting a hydroxy-functional starter, generally of low molecular weight, i.e., below 200 g/mol, such as butanol, allyl alcohol, propylene glycol or glycerol with an alkylene oxide such as ethylene oxide, propylene oxide, butylene oxide or a mixture of different alkylene oxides in the presence of the alkaline catalyst to afford a polyoxyalkylene polyether. The strongly alkaline reaction conditions in this so-called living polymerization promote various side reactions. The compounds of formulae (IV) may also be produced by double metal cyanide catalysis. Polyethers prepared by double metal cyanide catalysis generally have a particularly low content of unsaturated end groups of no more than 0.02 milliequivalents per gram of polyether compound (meq/g), preferably no more than 0.015 meq/g, more preferably no more than 0.01 meq/g (test method ASTM D2849-69), comprise distinctly fewer monools and generally have a low polydispersity of less than 1.5. The polydispersity (PD) may be determined by a method known per se to those skilled in the art by determining by gel permeation chromatography (GPC) both the number-average molecular weight (Mn) and the weight-average molecular weight (Mw). The polydispersity is defined by PD=Mw/Mn. The production of such polyethers is described in U.S. Pat. No. 5,158,922 and EP-A 0 654 302, for example.

Irrespective of the preparative route, compounds of formula (IV) preferably having a polydispersity Mw/Mn of from 1.0 to 1.5, preferably from 1.0 to 1.3, are preferentially suitable.

Compounds from compound class I that may be employed in the process according to the invention include all at least dinuclear platinum complex compounds. Preferably employed compounds from compound class I are di-µ-halogenobis(1,2-η)alkeneplatinum(II) halides, preferably di-µ-chlorobis(1,2-η)alkeneplatinum(II) chlorides and more preferably di-µ-chlorobis(1,2-η)cyclohexeneplatinum(II) chloride. The relevant complex compounds are obtainable from Johnson Matthey or Heraeus, for example. Johnson Matthey also refers to the complex as Pt-92 [PtCl$_2$(cyclohexene)]$_2$ according to handbook of pharmaceutical catalysis, page 46 (2009) and Heraeus refers to it as di-µ-chlorobis[chloro(cyclohexene)platinum(II)], CAS 12176-53-3. Alfa Aesar markets di-µ-chlorodichlorobis(cyclohexene)diplatinum(II) under CAS 60134-75-0.

When the employed compounds from compound class III are compounds that are gaseous or solid at a pressure of 101 325 Pa and a temperature of 23° C., for example ethylene, propylene and or butylene/trans-stilbene, it may be advantageous for the first step to comprise adding together these compounds from compound class III with the compounds from compound class II. When the employed compounds from compound class III are compounds that are liquid at a pressure of 101 325 Pa and a temperature of 23° C., it is preferable when the first step comprises adding together the compounds, preferably with stirring, with the compound(s) from compound class I.

The addition of the remaining compound class to the mixture obtained in the first step is preferably carried out with stirring.

The sequence of these procedures must be strictly adhered to since otherwise platinum precipitation may result in the formation of platinum preparations having impaired activity and/or in particular more or less coloration and whose appearance indicates insufficient storage stability of the preparations.

The amount of compounds from compound class III employed in the process according to the invention is preferably selected such that the total molar amount of olefinic unsaturations, in particular of effective olefinic unsaturations (i.e. those that are nonconjugated), in the preparation is at least double to 200 times, preferably at least 3 to 150 times and most preferably at least 4 to 40 times the total molar amount of platinum present in the preparation. The total molar amount of olefinic unsaturations in the preparation is equal to the sum of the olefinic unsaturations introduced via the compounds from compound class I (proportion of cyclohexene when di-µ-chlorobis[chloro(cyclohexene)platinum(II)] is employed as compound from compound class I) plus the sum of the olefinic unsaturations introduced via the compounds from compound class III.

As stated hereinabove, it is possible in accordance with the invention, albeit less preferred, to initially add together, and in doing so ideally dissolve, one or more platinum (II) compounds as compound(s) from compound class I with one or more compound(s) from compound class II comprising no olefinic unsaturation and to subsequently treat the resulting mixture with one or more olefinically at least monounsaturated compound(s) comprising fewer than two oxygen atoms as compound(s) from compound class III. This procedure is less preferred since, prior to the addition of the olefinically unsaturated compound(s) from compound class III, a less stable system prone to platinum precipitation is formed (see Example 1) which, in order to avoid the precipitation, needs to be treated as quickly as possible with a compound from compound class III (Example 7, preparation of di-µ-chlorobis[chloro(cyclohexene)platinum(II)]-initially in butyl diglycol with subsequent treatment with ethylene).

Also possible and in accordance with the invention, albeit less preferred, is a procedure where one or more platinum(II) compounds as compounds from compound class I is initially treated with one or more compound(s) from compound class III, namely, with the olefinically unsaturated compounds comprising at least one olefinic unsaturation and fewer than two oxygen atoms per molecule, and subsequently admixed with one and/or more compound(s) from compound class II, in particular those comprising no olefinic unsaturation. The practical limitations of this less preferred embodiment result from, inter alia, the phases of matter in the temperature range of from 23° C. to 40° C. of the components from the compound classes I and III that are to be combined, for example Pt92 (solid) plus ethylene (gaseous) or else Pt92 (solid) plus trans-stilbene (solid). Even in the case of the compounds from compound class III, which are liquid in the temperature range of from 23° C. to 40° C., the experimental observations show very limited solubility of platinum(II) compounds of the Zeise's salt dimer type (for example Pt92) in purely olefinically unsaturated compounds comprising at least one olefinic unsaturation and fewer than two oxygen atoms and in particular comprising no hydroxy/hydroxyalkyl group.

Less problematic, and thus given particular preference in the context of the teaching of the invention, is a procedure comprising initially adding together, and in doing so ideally dissolving, one or more platinum (II) compounds as compound(s) from compound class I with one or more compound(s) from compound class II comprising an olefinic unsaturation and subsequently treating the resulting mixture with one or more olefinically at least monounsaturated compound(s) comprising fewer than two oxygen atoms as compound(s) from compound class III. The fact that the olefinic unsaturation is present even at the point in time of preparing the premixture of compound(s) from compound class I with one or more compound(s) from compound class II appears to remedy the tendency of the system towards undesired platinum precipitation.

The production according to the invention of the preparations according to the invention is preferably carried out at a temperature of from 15° C. to 60° C., preferably from 25° C. to 40° C.

The process according to the invention makes it possible to obtain the preparations according to the invention which are described hereinbelow.

The preparations according to the invention comprising one or more platinum(II) compounds as compound(s) from compound class V and one or more compounds comprising carbon atoms, hydrogen atoms and at least two oxygen atoms and optionally one or more olefinic unsaturations, preferably no olefinic unsaturations, as compound(s) from compound class II, and one or more olefinically unsaturated compound(s) comprising at least one olefinic unsaturation and fewer than two oxygen atoms as compound(s) from compound class III comprise as compound(s) from compound class V one or more platinum complex compounds of formula (X)

[olefin1]$_x$[olefin2]$_y$Pt$^{2+}$Hal$^-_2$, where Hal=F, Cl, Br or I, x=1 or 2, y=0 or 1, olefin1=compound comprising at least one olefinic unsaturation and preferably no silicon atom, olefin2=compound comprising an olefinic unsaturation and preferably no silicon atom, with the proviso that when olefin1 comprises at least two olefinic unsaturations, x=1, and x+y=1, and when olefin1 comprises only one olefinic unsaturation, x+y=2, and with the proviso that the total molar amount of olefinic unsaturations is 2 to 200 times, by preference 3 to 150 times and preferably 4 to 40 times the total molar amount of platinum present in the preparation. Preferred platinum complex compounds are those arising from the above described preferred embodiments and preferably from the combination of the preferred embodiments for Hal, x, y, olefin1 and olefin2. Particularly preferred preparations are those comprising the platinum complex compound of formula (X) where Hal=Cl, olefin1=ethylene, olefin2=cyclohexene and x and y=1. When the preparation according to the invention comprises cyclohexene as a compound having an olefinic unsaturation the molar content of cyclohexene in the preparation is at least equal to the molar platinum concentration.

The preparation according to the invention preferably comprises as compounds from compound classes II and III the compounds described as preferable in the above described process according to the invention and combinations of these preferred compounds. Particularly preferred preparations according to the invention are those comprising as compounds from compound class II compounds comprising no olefinic unsaturation, preferably butyl diglycol, dipropylene glycol and/or propylene glycol, and as compounds from compound classes III ethylene and/or cyclohexene.

Preferred preparations according to the invention are those having a platinum concentration of from 0.1 to 1.5 weight percent and preferably from 0.5 to 1 weight percent of platinum based on the preparation.

Preferred preparations according to the invention are those comprising less than 5 mol %, preferably less than 0.5 mol %, of elemental platinum based on the total amount of platinum. Particular preference is given to preparations according to the invention comprising no detectable amounts of elemental platinum and/or platinum (0) (complex) compounds.

The preparations according to the invention preferably have a proportion of all compounds from compound class II and compound class III in the total preparation of from 98.5 to 99.9 wt %, preferably from 99.0 to 99.5 wt %.

The components in the preparation according to the invention are preferably homogeneously distributed. The preparation may, for example, be in the form of a solution, suspension, dispersion or paste or else it may consist of mixtures of these phases.

The preparations according to the invention may be employed in a process where compounds comprising H—Si groups are reacted with compounds comprising olefinic double bonds. These preparations according to the invention are preferably employed as a catalyst/catalyst preparation. The process is preferably what is known as a hydrosilylation process. Suitable silanes or siloxanes comprising SiH groups are described in "Chemie and Technologie der Silicone", Verlag Chemie, 1960, for example.

The use according to the invention preferably employs as H—Si group-bearing compounds monomeric silanes, for example $R_3SiH$; $R_2SiH_2$; $RSiH_3$;

cyclic silanes, for example $(RHSiO)_4$; $(RHSiO)_3$;

linear or branched oligomeric or polymeric siloxanes such as $R_3SiO$—$(R_2SiO$—$)_a(RSi(H)O$—$)_bSiR_3$, where a≥0 and b≥1;

$HR_2SiO$—$(R_2SiO$—$)_c(RSi(H)O$—$)_dSiR_2H$, where c and d≥0;

compounds of general formula (III)

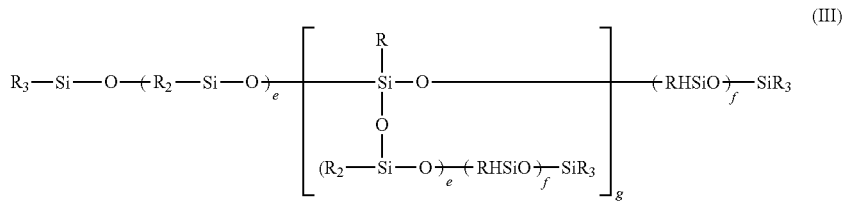

where
e=≥0,
f=≥1 and
g=≥1,
R are identical or different groups that do not impede the addition reaction, such as 1 to 8 carbon atom-comprising alkyl groups; substituted 1 to 8 carbon atom-comprising alkyl groups, such as a 3-chloropropyl group, 1-chloromethyl group, 3-cyanopropyl group; aryl groups, such as a phenyl group; aralkyl groups, such as a benzyl group; alkoxy or alkoxyalkyl groups, such as an ethoxy or ethoxypropyl group.

The process according to the invention preferably employs as compounds comprising olefinic double bonds compounds of formulae

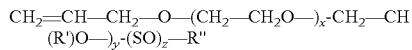

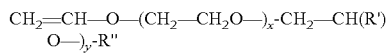

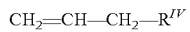

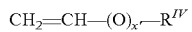

where
x=0 to 100,
x'=0 or 1,
y=0 to 100,
z=0 to 100,
R' is an optionally substituted 1 to 4 carbon atom-comprising alkyl group and
R" is a hydrogen radical or a 1 to 4 carbon atom-comprising alkyl group; the group —C(O)—R'" where R'"=alkyl radical; the group —CH$_2$—O—R'; an alkylaryl group, such as a benzyl group; the group —C(O)NH—R',
R$^{IV}$ is an optionally substituted hydrocarbon radical comprising from 7 to 47, preferably from 13 to 37, carbon atoms,
SO is the radical C$_6$H$_5$—CH(-)—CH$_2$—O— (styrene oxide radical).

The use according to the invention preferably comprises adding an amount of the preparation according to the invention to the reaction mixture such that the amount of platinum is from 1 to 100 wppm (mass ppm) based on the reaction mixture.

The process according to the use according to the invention may be carried out as described in EP 1520870 A1. The process may in particular be carried out under the conditions cited therein.

The processes made accessible by the use according to the invention are suitable, for example, for preparing SiC-bonded systems which are used in the field of polyurethane foam stabilizers (e.g.: hot-cure flexible foam, rigid foam, cold-cure foam, ester foam, etc.), which are used as release agents (silicone waxes, radiation-curing systems such as silicone acrylates for example, etc.), which are used in coatings additives as antifoams, deaerators, lubricant and leveling additives, as antigraffiti additives, in applications of wetting agents, in cosmetic formulations for thickeners, emulsifiers, etc.

The present invention is elucidated in more detail using the examples which follow, without any intention that the invention be restricted to these examples. The percentage SiH conversions reported in the examples are determined indirectly by treating the obtained reaction product with sodium butoxide in n-butanol and determining by volumetric means the amount of hydrogen that can still be cleaved off.

Example 1 (Noninventive)

A platinum metal catalyst preparation of di-μ-chlorobis [chloro(cyclohexene)platinum(II)] in butyl diglycol having a platinum concentration of 0.6 wt % was prepared as follows: 4.9457 g of butyl diglycol were initially charged into a glass vessel sealable with a rubber septum and admixed with (0.0543 g) of a pulverulent di-μ-chlorobis [chloro(cyclohexene)platinum(II)] catalyst complex. The vessel was hermetically sealed with septum cap. The vessel contents were homogenized by shaking. The platinum metal catalyst preparation was a clear, slightly yellowish solution.

One portion of the catalyst preparation was used directly in Example 2 and another portion was used in Example 3 after four weeks of storage in the sealed glass vessel in the absence of light at 22° C. Even after one day of storage, a thick precipitate of finely divided black noble metal was observed at the bottom of the glass vessel.

Example 2 (Noninventive)

A 500 ml four-necked round-bottom flask fitted with a KPG stirrer, reflux cooler and internal thermometer was initially charged with 60 g of a pendant hydrosiloxane of general formula

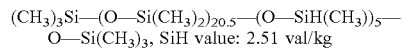

together with 161.3 g of a polyether of average formula

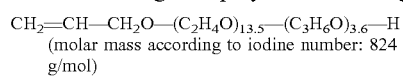
(molar mass according to iodine number: 824 g/mol)

with stirring and quickly heated to 70° C. At 50° C., 4 wppm of platinum based on the total batch of the platinum metal catalyst preparation from Example 1 produced immediately beforehand were added. After a reaction time of two hours, the SiH conversion determined by gas-volumetric means (determined by decomposition of an aliquot withdrawn from the reaction batch by addition of sodium butoxide solution using a gas burette) was 91.9%. After 4 hours, the SiH conversion determined by gas-volumetric means had reached 99.3%. After cooling to 22° C., a clear, slightly yellowish polyether siloxane was obtained.

Example 3 (Noninventive)

While maintaining the experimental parameters referred to in Example 2, a further hydrosilylation reaction was carried out wherein at 50° C. a volume of the above described platinum metal catalyst preparation from Example 1 stored for 4 weeks and comprising arithmetically 4 wppm of platinum based on the total batch was added. To this end, the finely divided platinum metal previously deposited in the septum glass vessel was whirled up and an aliquot of this suspension was then withdrawn and added to the reaction batch using a syringe.

After two hours, the reaction catalysed in this fashion had achieved an SiH conversion determined by gas-volumetric means of 11.5%. After 4 hours, the gas-volumteric SiH conversion was 50.7% and, after 5 hours, the conversion was 78.1%. The batch was terminated and after cooling to 22° C. a very cloudy reaction product was isolated.

Example 4 (Inventive)

A platinum metal catalyst preparation of di-μ-chlorobis [chloro(cyclohexene)platinum(II)] in a solution of ethylene in butyl diglycol (0.0212 g of ethylene in 5.0 g of butyl diglycol) having a platinum concentration of 0.6 wt % was prepared as follows: In a tared glass vessel sealed with a rubber septum, 4.9457 g of butyl diglycol were treated with an ethylene gas stream at 22° C. using two injection needles serving as gas inlet and outlet so that a total of 0.0212 g of ethylene dissolved therein. The septum cap was removed, 0.0543 g of the pulverulent di-μ-chloro-bis[chloro(cyclohexene)platinum(II)] catalyst complex was quickly weighed in and the vessel was hermetically sealed with a new septum cap. The vessel contents were homogenized by shaking. The platinum metal catalyst preparation was a clear, homogeneous, slightly yellowish solution.

One portion of the catalyst preparation was used directly in Example 5 and another portion was used in Example 6 after four weeks of storage in the sealed glass vessel in the absence of light at 22° C. Even after four weeks of storage, the platinum metal catalyst preparation was a clear, homogeneous slightly yellowish solution.

Example 5 (Inventive)

A 500 ml four-necked round-bottom flask fitted with a KPG stirrer, reflux cooler and internal thermometer was initially charged with 60 g of a pendant hydrosiloxane of general formula

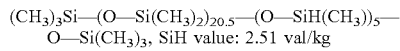
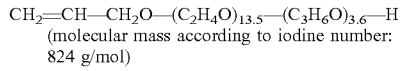

together with 161.3 g of a polyether of average formula $CH_2=CH-CH_2O-(C_2H_4O)_{13.5}-(C_3H_6O)_{3.6}-H$
(molecular mass according to iodine number: 824 g/mol)

with stirring and quickly heated to 70° C. At 50° C., 4 wppm of platinum based on the total batch of the platinum metal catalyst preparation from Example 4 produced immediately beforehand were added.

After a reaction time of two hours, the SiH conversion determined by gas-volumetric means (determined by decomposition of an aliquot using sodium butoxide solution and a gas burette) was 92.6%. After 4 hours, the SiH conversion determined by gas-volumetric means was quantitative (100%). After cooling to 22° C., a clear, slightly yellowish polyether siloxane was obtained.

Example 6 (Inventive)

While maintaining the experimental parameters cited in Example 5 a further hydrosilylation reaction was carried out, wherein at 50° C. 4 wppm of platinum based on the total batch of the platinum metal catalyst preparation described in Example 4 stored for 4 weeks were added. After 2 hours, the reaction batch catalyzed using this solution achieved an SiH conversion determined by gas-volumetric means of 93.4%. After 4 hours, the SiH conversion was virtually quantitative (99.3%). The reaction batch was cooled to 22° C. and a clear, slightly yellowish polyether siloxane was isolated.

The inventive examples show that the process according to the invention for producing platinum metal catalyst preparations makes it possible to produce preparations that have markedly improved storage stability compared to preparations prepared with a prior art process.

Example 7 (Inventive)

Similarly to Example 1, a platinum metal catalyst preparation of di-μ-chloro-bis[chloro(cyclohexene)platinum(II)] in butyl diglycol having a platinum concentration of 0.6 wt % was prepared as follows: 4.9457 g of butyl diglycol were initially charged into a glass vessel sealable with a rubber septum and admixed with 0.0543 g of a pulverulent di-μ-chloro-bis[chloro(cyclohexene)platinum(II)] catalyst complex. The vessel was hermetically sealed with a septum cap. The vessel contents were homogenized by shaking. The platinum metal catalyst preparation was a clear, slightly yellowish solution.

1 hour later, ethylene gas was passed through the solution which was still free of platinum precipitate at 22° C. using two injection needles serving as gas inlet and outlet so that a total of 0.0123 g of ethylene was dissolved therein.

One portion of the catalyst preparation was used directly in Example 8 and another portion was used in Example 9 after four weeks of storage in the sealed glass vessel in the absence of light at 22° C. Even after four weeks of storage, the platinum metal catalyst preparation was a clear, homogeneous slightly yellowish solution.

Example 8 (Inventive)

A 500 ml four-necked round-bottom flask fitted with a KPG stirrer, reflux cooler and internal thermometer was initially charged with 60 g of a pendant hydrosiloxane of general formula

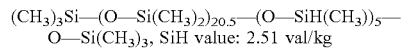
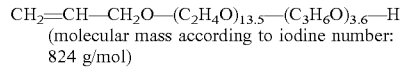

together with 161.3 g of a polyether of average formula $CH_2=CH-CH_2O-(C_2H_4O)_{13.5}-(C_3H_6O)_{3.6}-H$
(molecular mass according to iodine number: 824 g/mol)

with stirring and quickly heated to 70° C. At 50° C., 4 wppm of platinum based on the total batch of the platinum metal catalyst preparation from Example 7 produced immediately beforehand were added.

After a reaction time of two hours, the SiH conversion determined by gas-volumetric means (determined by decomposition of an aliquot using sodium butoxide solution and a gas burette) was 91.7%. After 4 hours, the SiH conversion determined by gas-volumetric means was quantitative (100%). After cooling to 22° C., a clear, slightly yellowish polyether siloxane was obtained.

Example 9 (Inventive)

While maintaining the experimental parameters cited in Example 8 a further hydrosilylation reaction was carried out, wherein at 50° C. 4 wppm of platinum based on the total batch of the platinum metal catalyst preparation described in Example 7 stored for 4 weeks were added.

After 2 hours, the reaction batch catalyzed using this solution achieved an SiH conversion determined by gas-volumetric means of 90.4%. After 4 hours, the SiH conversion was 99.1% and after 5 hours the conversion was quantitative. The reaction batch was cooled to 22° C. and a clear, slightly yellowish polyether siloxane was isolated.

While the present invention has been particularly shown and described with respect to preferred embodiments, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed as new is:

1. A preparation comprising one or more platinum(II) compounds as compound(s) from compound class IV and one or more compounds comprising carbon atoms, hydrogen atoms and at least two oxygen atoms and optionally one or more olefinic unsaturations as compound(s) from compound class II, and one or more olefinically unsaturated compound(s) comprising at least one olefinic unsaturation and fewer than two oxygen atoms as compound(s) from compound class III, wherein said preparation comprises as compound(s) from compound class IV platinum complex compounds

[olefin1]$_x$[olefin2]$_y$Pt$^{2+}$Hal$^-$$_2$, wherein
Hal=Cl,
x=1 or 2,
y=0 or 1,
olefin1=ethylene,
olefin2=cyclohexene,
wherein when olefin 1 comprises only one olefinic unsaturation, x+y=2, in each case with the proviso that the total molar amount of olefinic unsaturations is 2 to 200 times the total molar amount of platinum present in the preparation.

2. The preparation according to claim 1, wherein said preparation is obtained by the process comprising:
contacting at least one compound from each of compound classes II and III with one or more dinuclear platinum (II) compound(s) as compound(s) from compound class 1, wherein said contacting comprises,
in a first step, preparing a mixture by adding together at least two compounds selected from two different compound classes, and,
in a second step, admixing the mixture obtained in the first step with one or more compounds of the absent compound class.

3. A process for producing preparations comprising one or more mononuclear platinum complex compounds of formula (X)

[olefin1]$_x$[olefin2]$_y$Pt$^{2+}$Hal$^-$$_2$, where
Hal=Cl,
x=1 or 2,
y=0 or 1,
olefin1=ethylene,
olefin2=cyclohexene,
wherein when olefin 1 comprises only one olefinic unsaturation, x+y=2, one or more compounds comprising carbon atoms, hydrogen atoms and at least two oxygen atoms as compound(s) from compound class II,
and one or more olefinically unsaturated compound(s) selected from olefin1 and olefin2 as compound(s) from compound class III, said process comprising:
contacting at least one compound from each of compound classes II and III with one or more dinuclear platinum (II) compound(s) as compound(s) from compound class 1, wherein said contacting comprises, in a first step, preparing a mixture by adding together at least two compounds selected from two different compound classes, and, in a second step, admixing the mixture obtained in the first step with one or more compounds of the absent compound class.

4. The process according to claim 3, wherein in said first step said mixture of compounds is from compound classes I and III, and in said second step a compound(s) from compound class II is employed.

5. The process according to claim 3, wherein in said first step said mixture of compounds is from compound classes II and III, and in said second step a compound(s) from compound class I is employed.

6. The process according to claim 3, wherein said first step does not comprise preparing a mixture comprising the compounds from compound classes I and II.

7. The process according to claim 3, wherein the proportion of compounds from compound class 1 based on the sum of the employed compounds from compound classes I, II, and III is from 0.1 to 50.0 wt %.

8. The process according to claim 3, wherein an amount of compounds of compound class III is employed such that the preparation has an olefinic unsaturation content of at least 0.05 g of iodine/1 00 g of preparation, corresponding to at least 0.002 meq/g.

9. The process according to claim 8, wherein compounds from compound class II comprise compounds of formula (IV)

A[-O—(CH$_2$—CHR'—O—)$_m$-(CH$_2$—CH$_2$—O—)$_n$-(CH$_2$—CH(CH$_3$)—O—)$_o$-Z]$_a$      (IV)

where
A is either hydrogen or an at least one carbon atom-comprising saturated or unsaturated organic radical,
R' is independently at each occurrence a saturated 2-18 carbon atom-comprising alkyl group or an aromatic radical,
Z is either hydrogen, a linear or branched, saturated or unsaturated 1-18 carbon atom-comprising hydrocarbon radical, or
the radical of an organic acid of formula —C(=O)—Z$_E$, where Z$_E$ is an organic radical, or the radical of formula —C(=O)—O—Z$_C$, where Z$_C$ is an organic radical,
m equals 0 to 50,
n equals 0 to 250, o equals 0 to 250 a equals 1 to 8, with the proviso that m, n and o sum to no less than 1.

10. The process according to claim 9, wherein said compound from compound class 1 is di-µ-chlorobis(1,2-η) cyclohexeneplatinum(II) chloride.

11. The process according to claim 10, wherein compounds from compound class II having a weight-average molar mass of from 76 to 10 000 g/mol are employed.

12. The process according to claim 11, wherein compounds from compound class II compounds derived from formula (VI)

$$A[-OH]_a \quad (VI)$$

where the radical A derives from compounds selected from the group consisting of mono- and polyfunctional monomeric, oligomeric and polymeric alcohols, phenols, carbohydrates and carbohydrate derivatives are employed.

13. The process according to claim 12, wherein the radical A derives from one or more alcohols selected from the group consisting of butanol, 1-hexenol, octanol, dodecanol, stearyl alcohol, vinyloxybutanol, 2-ethylhexanol, cyclohexanol, benzyl alcohol, ethylene glycol, propylene glycol, di-, tri- and polyethylene glycol, 1,2-propylene glycol, di- and polypropylene glycol, 1,4-butanediol, 1,6-hexanediol, trimethylolpropane, glycerol, pentaerythritol, allyl alcohol, vinyl alcohol, and sorbitol or from hydroxyl group-bearing compounds based on natural products.

14. A method comprising reacting compounds comprising H—Si groups with compounds comprising olefinic double bonds in the presence of a preparation according to claim 1.

15. The method according to claim 14, wherein the compounds comprising H—Si groups are selected from
monomeric silanes;
cyclic silanes;
linear or branched oligomeric or polymeric siloxanes selected from
$R_3SiO$—$(R_2SiO$—$)_a(RSi(H)O$—$)_bSiR_3$, where a≥0 and b≥1;
$HR_2SiO$—$(R_2SiO$—$)_c(RSi(H)O$—$)_dSiR_2H$, where c and d≥0;
compounds of general formula (III)

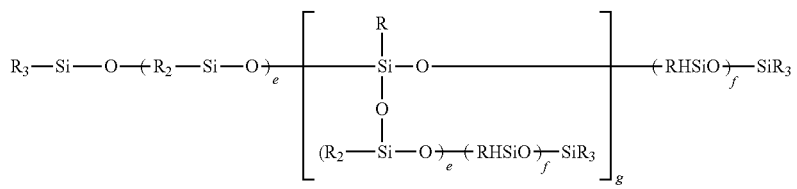

where
e=≥0
f=≥1 and
g≥1,
R are identical or different groups comprising 1 to 8 carbon atom-comprising alkyl groups; substituted 1 to 8 carbon atom-comprising alkyl groups; aryl groups; aralkyl groups; alkoxy or alkoxyalkyl groups or compounds comprising olefinic double bonds of formulae $$CH_2=CH-CH_2-O-(CH_2-CH_2O-)_x-CH_2-CH(R')O-)_y-(SO)_z-R''$$

$$CH_2=CH-O-(CH_2-CH_2O-)_x-CH_2-CH(R')O-)_y-R''$$

$$CH_2=CH-CH_2-R^{IV}$$

$$CH_2=CH-(O)_{x'}-R^{IV}$$

where
x=0 to 100,
x'=0 or 1,
y=0 to 100,
z=0 to 100,
R'' is an optionally substituted 1 to 4 carbon atom-comprising alkyl group, and
R''' is a hydrogen radical or a 1 to 4 carbon atom-comprising alkyl group; the group —C(O)—$R^v$ where $R^v$=alkyl radical; the group —CH2-0-R''; an alkylaryl group; the group —C(O)NH—R'',
$R^{IV}$ is an optionally substituted hydrocarbon radical comprising from 7 to 47 carbon atoms,
SO is the radical $C_6H_5$—CH(-)—$CH_2$—O— (styrene oxide radical).

16. The method according to claim 15, wherein an amount of the preparation that is added to the reaction mixture is such that the total concentration of platinum is from 1 to 100 wppm based on the reaction mixture.

17. The preparation according to claim 1, wherein compounds from compound class II comprise compounds of formula (IV)

$$A[-O-(CH_2-CHR'-O-)_m-(CH_2-CH_2-O-)_n-(CH_2-CH(CH_3)-O-)_o-Z]_a \quad (IV)$$

where
A is either hydrogen or an at least one carbon atom-comprising saturated or unsaturated organic radical,
R' is independently at each occurrence a saturated 2-18 carbon atom-comprising alkyl group or an aromatic radical,
Z is either hydrogen, a linear or branched, saturated or unsaturated 1-18 carbon atom-comprising hydrocarbon radical, or
the radical of an organic acid of formula —C(=O)—$Z_E$, where $Z_E$ is an organic radical, or the radical of formula —C(=O)—O—$Z_C$, where $Z_C$ is an organic radical,
m equals 0 to 50,
n equals 0 to 250,
o equals 0 to 250
a equals 1 to 8,
with the proviso that m, n and o sum to no less than 1.

18. The preparation according to claim 1, wherein compounds from compound class II compounds derived from formula (VI)

$$A[-OH]_a \quad (VI)$$

wherein the radical A derives from compounds selected from the group consisting of mono- and polyfunctional monomeric, oligomeric and polymeric alcohols, phenols, carbohydrates and carbohydrate derivatives.

19. The preparation according to claim 18, wherein the radical A derives from one or more alcohols selected from the group consisting of butanol, 1-hexenol, octanol, dodecanol, stearyl alcohol, vinyloxybutanol, 2-ethylhexanol, cyclohexanol, benzyl alcohol, ethylene glycol, propylene glycol, di-, tri- and polyethylene glycol, 1,2-propylene glycol, di- and polypropylene glycol, 1,4-butanediol, 1,6-hexanediol, trimethylolpropane, glycerol, pentaerythritol, allyl alcohol, vinyl alcohol, and sorbitol or from hydroxyl group-bearing compounds based on natural products.

* * * * *